United States Patent [19]

Hattori et al.

[11] 4,130,797
[45] Dec. 19, 1978

[54] GAS COMPONENT SENSING APPARATUS

[75] Inventors: Tadashi Hattori, Okazaki; Hiroaki Yamaguchi, Aichi, both of Japan

[73] Assignee: Nippon Soken, Inc., Nishio, Japan

[21] Appl. No.: 853,830

[22] Filed: Nov. 21, 1977

[30] Foreign Application Priority Data

Nov. 25, 1976 [JP] Japan .................. 51/141883
Nov. 25, 1976 [JP] Japan .................. 51/141884

[51] Int. Cl.² ............................................. G01R 27/02
[52] U.S. Cl. .................. 324/65 P; 73/27 R; 338/34; 324/71 SN; 422/98
[58] Field of Search ............... 324/65 P, 65 R, 71 SN; 73/23, 27 R; 23/254 E, 232 E; 338/34; 340/237

[56] References Cited

U.S. PATENT DOCUMENTS

| 3,522,010 | 7/1970 | Archer | 23/254 E |
| 4,029,472 | 6/1977 | Micheli et al. | 23/254 E |

Primary Examiner—Stanley T. Krawczewicz
Attorney, Agent, or Firm—Cushman, Darby & Cushman

[57] ABSTRACT

In a gas component sensing apparatus a pair of thin film electrodes are arranged on opposite sides of a gas component sensor element, an electrical resistance of which varies in accordance with gas component in a gas under test. The change in the electrical resistance is taken out between a lead member and a housing through a first electrically conductive path which electrically connects one of the pair of electrodes to the lead member and a second electrically conductive path which electrically connects the other electrode to the housing.

3 Claims, 19 Drawing Figures

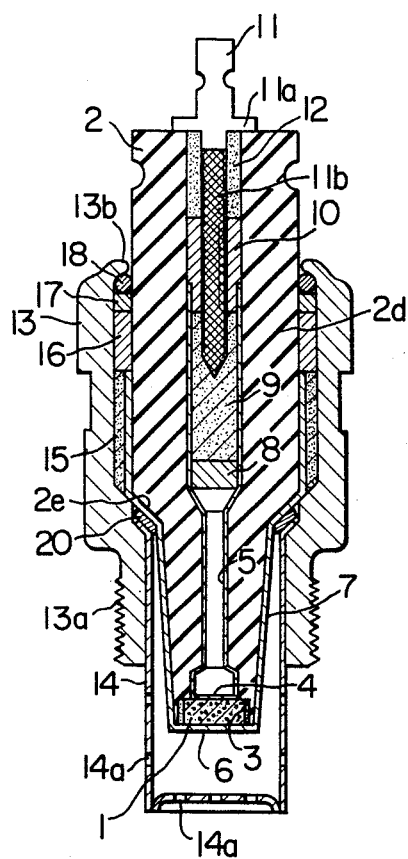
FIG. 1
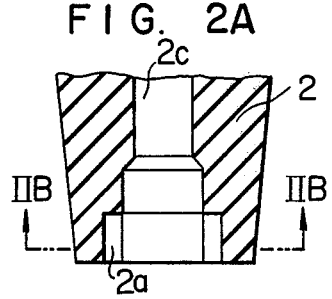
FIG. 2A
FIG. 2B
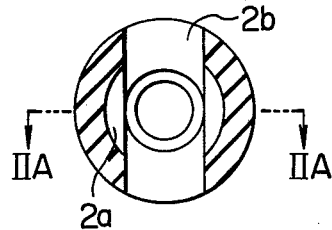
FIG. 3A
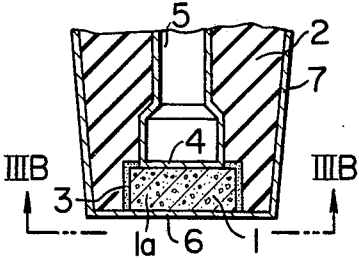
FIG. 3B
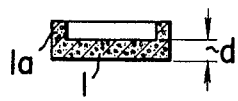
FIG. 4
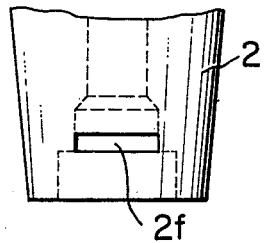
FIG. 5
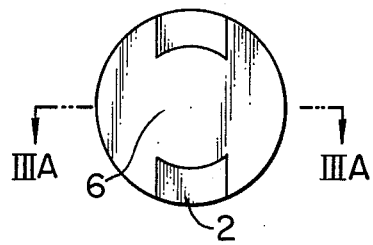

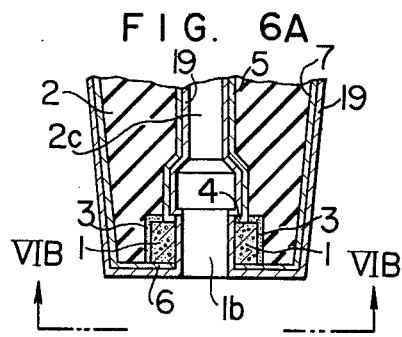
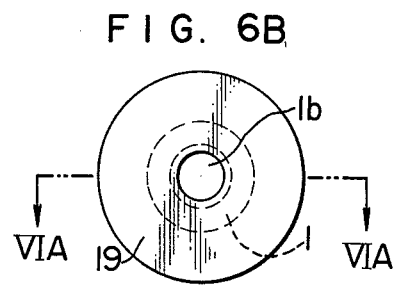
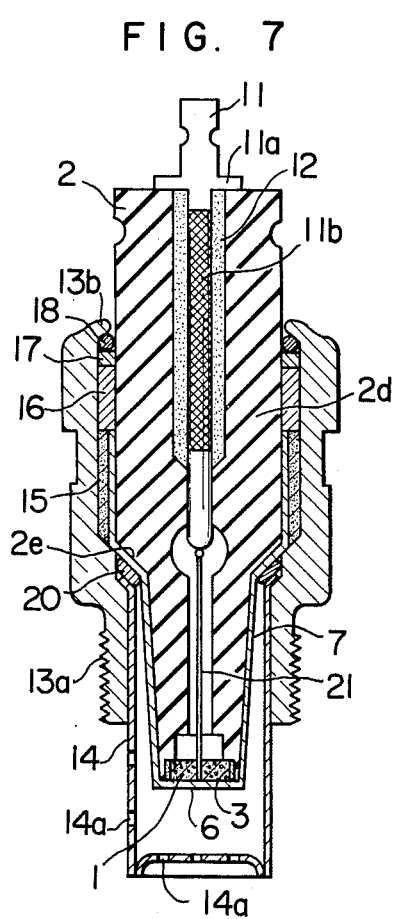
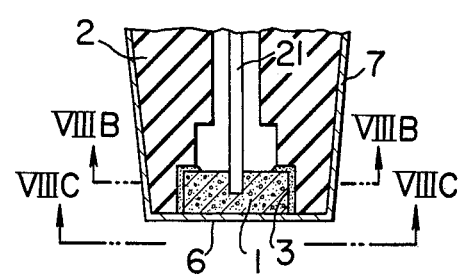
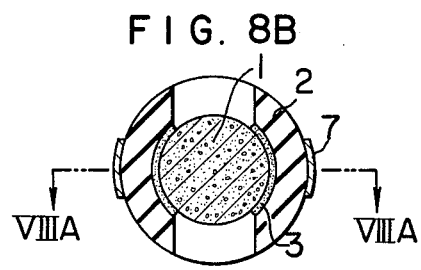
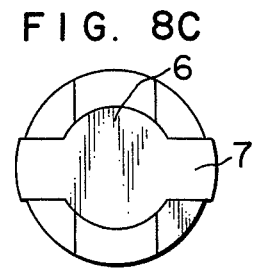

GAS COMPONENT SENSING APPARATUS

BACKGROUND OF THE INVENTION

The present invention relates to a gas component sensing apparatus for sensing, for example, an oxygen concentration of exhaust gases emitted from a vehicle engine.

One of the prior art apparatuses of this type uses a metal oxide such as titanium oxide, an electrical resistance of which changes in accordance with the change in gas component density in a gas under test such as exhaust gas.

In a basic structure thereof, a pair of rod electrodes made of noble metal (Pt) are connected to a gas component sensor element mode of titanium oxide, the pair of electrodes are inserted in a holder made of heat resistance, electrically insulative metal oxide and the electrodes are fixed to lead members which are fixed to the holder.

The prior art sensing apparatus of the type described above, however, has the following drawbacks:

(1) In a two-wire sensing apparatus having a pair of electrodes, two electrodes and two lead members must be inserted in a holder of limited size, and hence the distance between the electrodes and the distance between the lead members are necessarily very short. Accordingly, holes must be formed in the holder very carefully to prevent the shortcircuit among the components.

(2) Since the distance between the lead members is short, the lead members cannot be connected to a connector of a control circuit unless a small size connector is used. Such a small size connector requires a complex construction and increases cost.

(3) As the connector becomes small and complex, it is difficult to design a connector which improves resistance to vibration, water proofing and resistance to heat at the junction of the connector and the lead members.

SUMMARY OF THE INVENTION

It is an object of the present invention to overcome the above drawbacks and provide a gas component sensor of a novel structure in which a pair of thin film electrodes are arranged on opposite sides of a gas component sensor element and an electrical output is taken through first and second electrically conductive paths connected to the thin film electrodes.

BRIEF DESCRIPTION OF THE DRAWINGS

FIG. 1 shows a sectional view of a gas component sensing apparatus of the present invention;

FIG. 2A shows an enlarged sectional view, taken along a line IIA-IIA in FIG. 2B, of a holder shown in FIG. 1;

FIG. 2B shows a sectional view taken along a line IIA—IIA in FIG. 2A;

FIG. 3A shows an enlarged sectional view, taken along a line IIIA—IIIA in FIG. 3B, of the gas component sensing apparatus of FIG. 1;

FIG. 3B shows a bottom view when viewed in a direction designated by a line IIIB—IIIB in FIG. 3A;

FIG. 4 is a sectional view showing a modification of a solid electrolyte;

FIG. 5 is a partial front view, in an enlarged scale, showing a modification of a holder;

FIG. 6A is a partial sectional view, in an enlarged scale, taken along a line VIA—VIA in FIG. 6B, showing another embodiment of the present invention;

FIG. 6B shows a bottom view when viewed in a direction designated by a line VIB—VIB in FIG. 6A;

FIG. 7 is a sectional view showing another embodiment of the present invention;

FIG. 8 is a partial sectional view, in an enlarged scale, taken along a line VIIIA—VIIIA in FIG. 8B, showing a gas component sensing apparatus shown in FIG. 7;

FIGS. 8B and 8C show sectional view and bottom view, respectively, taken along a line VIIIB—VIIIB and viewed in a direction designated by a line VIIIC—VIIIC in FIG. 8A;

DESCRIPTION OF THE PREFERRED EMBODIMENTS

Figure 10A:
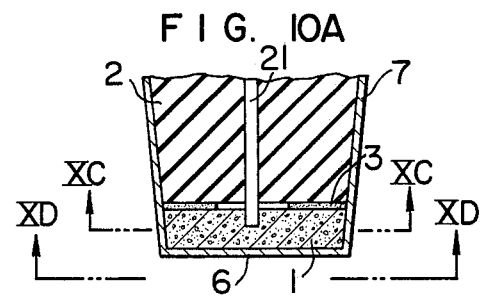
FIG. 10A is a partial sectional view, in an enlarged scale, taken along a line XA—XA in FIG. 10C, showing a gas component sensing apparatus using the holder shown in FIGS. 9A and 9B.

The present invention will now be described in detail in conjunction with the preferred embodiments thereof. Referring to FIGS. 1 to 3, numeral 1 denotes a gas component sensor element (solid electrolyte) whcih consists of a porous sintered body of transition metal oxide such as titanium oxide or metal oxide such as tin oxide, having an electrical resistance which varies with a gas component such as oxygen concentration in the exhaust gases. Numeral 2 denotes a holder made of heat resistive, electrically insulative metal oxide such as alumina ($\alpha$—$Al_2O_3$), having an arcuate stepped recess 2a at an end thereof and a radially extending groove 2b as best shown in FIGS. 2A and 2B. Through the groove 2b, exhaust gas is brought into contact with an inner surface (upper end surface in the drawing) of the gas component sensor element 1. An axial via-hole 2c is formed in the holder 2. The gas component sensor element (solid electrolyte) 1 of a circular configuration is housed in the stepped recess 2a of the holder 2 on one end side of the via-hole 2c, and bonded and fixed at a bonding area 1a by inorganic bond 3 such as borosilicate glass.

Platinum paste is applied over an area extending from the inner surface of the gas component sensor element 1 through the inner surface of the holder 2 on one side (bottom) of the via-hole 2c to the inner side on the other side (top), and the platinum paste is fired to form a thin platinum layer. That portion of the platinum layer which lies on the inner surface of the gas component sensor element 1 extends over entire inner surface to form a thin film electrode 4. That portion of the plantinum layer which extends from the inner surface of the holder 2 on one side of the via-hole 2c to the inner surface on the other side extends over the entire inner surface therebetween to form an electrically conductive path 5 which electrically connects the electrode 4 with a lead members 11 as described later. Similarly, platinum paste is applied over an area extending from an outer surface of the gas component sensor element 1 facing the inner surface thereof (lower end surface in the drawing) to a body 2d of the holder 2, and the platinum paste is fired to form a thin platinum layer. That portion of the platinum layer which lies over the outer surface of the gas component sensor element 1 extends over the entire outer surface to form a thin film electrode 6. That portion of the platinum layer which extends to the body 2d of the holder 2 extends over the entire outer periphery thereof to form an electrically conductive path 7 which electrically connects the electrode 6 with a housing 13 as described later.

Arranged intermediate of the through-hole 2c of the holder 2 are a washer 8 made of metal oxide such as alumina, conductive metal powder 9 made of copper, nickel or carbon and a ring 10 made of metal oxide such as alumina, and the lead member 11 made of conductive metal extends from the other side of the via-hole 2c of the holder 2 to the conductive metal powder 9. The lead member 11 is fixed by bond 12 such as borosilicate glass. The lead member 11 is comprised of a flange 11a and a knurled portion 11b. With this arrangement, the thin film electrode 4 of the gas component sensor element 1 is electrically connected to the lead member 11 through the electrically conductive path 5 and the conductive metal powder 9. Numeral 13 denotes the housing having a threaded portion 13a for attachment to an exhaust pipe (not shown). It is adapted to be fixed to the outer periphery of the holder 2 and made of heat resistive, electrically conductive metal. Numeral 14 denotes a protection cover made of heat resistive metal having a plurality of small openings 14a through which exhaust gas is transmitted. Inserted between the housing 13 and a tapered portion 2e at the intermediate portion of the holder 2 are a packing 20 and an end of the protection cover 14, and arranged between the housing 13 and the body 2d of the holder 2 are conductive metal powder 15 of copper, nickel or carbon, a spacer 16 made of stainless steel, a washer 17 made of heat resistive metal and a ring 18 made of soft metal such as nickel. The housing 13 and the holder 2 are fixed together by caulking a top portion 13b of the housing 13. With this arrangement, the thin film electrode 6 on the outer surface of the gas component sensor element 1 is electrically connected to the housing 13 through the electrically conductive path 7 and the conductive metal powder 15. Accordingly, the electrical resistance of the gas component sensor element 1 is taken across the lead member 11 and the housing 13.

The sensing apparatus thus constructed is fixed to the exhaust pipe (not shown) by means of the housing 13. The gas component sensor element 1 of the sensing apparatus exhibits the electrical resistance which changes in accordance with the change in the density of gas components ($CO$, $HC$, $H_2O_2$, etc.) in the exhaust gas which flows through the exhaust pipe and around the gas component sensor element 1. An electrical signal is taken across the lead member 11 and the housing 13 for application to a control circuit (not shown). As is well known, the temperature of the exhaust gas changes over a wide range. Thus, the gas component sensor element 1 and the end of the holder 2 for housing the gas component sensor element 1 are subjected to a heating-cooling cycle by the exhaust gas. However, since the gas component sensor element 1, the holder 2 and the bond 3 are all made of inorganic material and have substantially the same coefficient of thermal expansion, it is very rare that the gas component sensor element 1 peels off the recess 2a of the holder 2. Further, since that portion of the gas component sensor element 1 which is not exposed to the exhaust gas is surrounded by the inner wall of the stepped recess 2a of the holder 2, even if the gas component sensing apparatus is subjected to vibration, the inner wall of the recess 2a of the holder 2 acts against the force by the vibration which tends to move the gas component sensor element 1 so that the movement of the gas component sensor element 1 by the vibration can be prevented. Accordingly, the holding and fixing portion to the gas component sensor element 1 and the holder 2 shows a high resistance to vibration. Furthermore, since the gas component sensor element 1 is housed in the recess 2a of the holder 2, the thickness of the gas component sensor element 1 can be reduced by reducing the depth of the recess 2a of the holder 2. The thin gas component sensor element 1 can improve the response of the gas component sensor element 1 to the change of the gas component density. An embodiment of the sensor element constructed in this manner is shown in FIG. 4. In this embodiment, the portion 1a to which the bond is applied is made thicker to enhance the strength. The thickness d of the sensing portion is preferably in the order of 0.3 to 1.0 mm.

As described above in connection with the preferred embodiment, the formation of the pt thin film electrode 6 is very effective because a catalytic function by the thin film electrode 6 is expected. By the catalytic function, the air-fuel ratio vs electrical resistance characteristic of the exhaust gas changes stepwise (Z-shape) near the stoichiometric air-fuel ratio, eliminating the compensation of the electrical resistance to the exhaust gas temperature near the step in the characteristic.

FIG. 5 shows another embodiment of the present invention in which the groove 2b of the holder 2 in the previous embodiment has been replaced by a radially extending through-hole 2f having the same function as the groove 2b and a bonding area for the gas component sensor element 1 and the holder 2 extend around entire circumference of the gas component sensor element 1.

FIGS. 6A and 6B show a further embodiment of the present invention in which a through-hole 1b is formed in that portion of the gas component sensor element 1 which faces the through-hole 2c of the holder 2 so that the exhaust gas is brought into contact with the inner side of the gas component sensor element 1, that is, on the side of the thin film electrode 4, and a porous metal oxide coating 19 is formed on the surfaces of the thin film electrodes 4 and 6 and the electrically conductive paths 5 and 7. In the present embodiment, the metal oxide coating 19 may be made of $\gamma$-alumina and it protects the thin film electrodes 4 and 6 and the electrically conductive paths 5 and 7 from noxious material (phosphorus, lead, sulfur, etc.) in the exhaust gas.

Referring now to FIG. 7 and FIGS. 8A to 8C, there is shown another embodiment in which an electrode 21 at the top end of the gas component sensor element 1 is made of a conductive metal wire rather than the thin film as in the previous embodiment, and one end of the metal wire is buried in the gas. Component sensor element 1 while the other end thereof is electrically connected to the end of lead member 11 by laser spot welding. In the present embodiment, the electrically conductive path 7 for electrically connecting the electrode 6 with the housing 13 is a thin film metal strip layer.

Figure 9A:
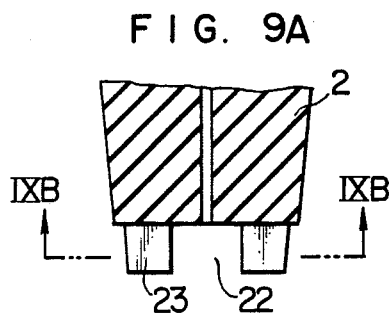
FIG. 9A is a partial sectional view, in an enlarged scale, taken along a line IXA—IXA in FIG. 9B, showing another embodiment of the holder of the present invention.
Figure 10B:
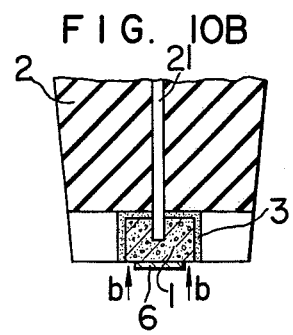
FIG. 10B shows a sectional view taken along a line XB—XB in FIG. 10C.
Figure 9B:
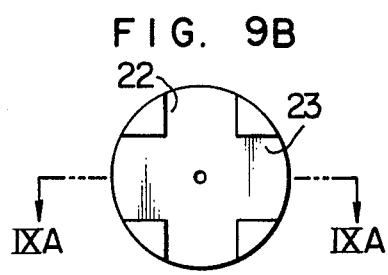
FIG. 9B shows a sectional view taken along a line IXB—IXB in FIG. 9A.
Figure 10C:
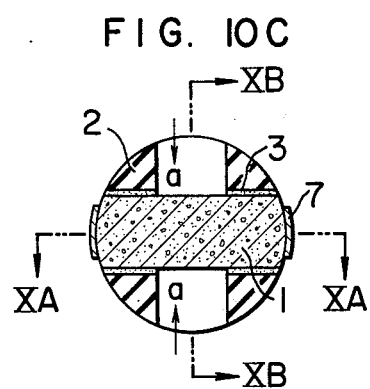
FIG. 10C shows a sectional view taken along a line XC—XC in FIG. 10A.
Figure 10D:
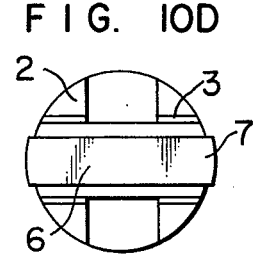
FIG. 10D shows a bottom view when viewed in a direction designated by a line XD—XD in FIG. 10A.

Referring to FIGS. 9A and 9B and FIGS. 10A to 10D, in which FIGS. 9A and 9B show sectional view of the holder 2, a radially extending recess 23 is formed at the bottom end of the holder 2 and a groove 22 which traverses the recess 23 is formed. As seen from FIGS. 10A to 10D, the square (parallelepiped) gas component sensor element (solid electrolyte) 1 is fitted in the recess 23 and fixed to the holder 2 by the bond 3 made of inorganic material. The thin film metal strip layer (electrode 6) is formed longitudinally on the outer surface of the solid electrolyte, and it is connected to the conductive strip path 7 for electrically connecting the metal strip layer 6 with the housing. As seen from FIG. 10D, the width of the electrode 6 is narrower than the width of the solid electrolyte 1. In the present embodiment, the exhaust gas passes through the groove 22 of the holder 2 and is brought into contact with the solid electrolyte 1 as shown by an arrow a as best shown in FIG. 10C. The exhaust gas is also brought into contact with the solid electrolyte 1 as shown by an arrow b in FIG. 10B. In this manner, the solid electrolyte 1 is exposed to the exhaust gas on its side surfaces and its bottom outer surface except that portion which is fitted in the holder 2. Accordingly, an excellent response is attained.

While platinum (Pt) has been shown in the above embodiments as the material for the thin film electrodes 4 and 6, the wire electrode 21 and the electrically conductive paths 5 and 7, rhodium (Rh), paladium (Pd) or an alloy thereof may be used.

Further, while the thin film electrodes 4 and 6 and the electrically conductive paths 5 and 7 have been shown to be formed by firing the platinum paste, they may be formed by sputtering, vacuum deposition or chemical deposition.

Furthermore, when the thin film electrodes 4 and 6 are formed on the entire inner and outer surfaces of the gas component sensor element 1 as in the case of the embodiments of FIGS. 1 to 6, the electrodes 4 and 6 must be porous. However, where the electrodes 4 and 6 are formed locally (in island shape), they need not be porous. The porous electrode is advantageous because it provides a larger catalyst active area. The metal oxides applicable to the gas component sensor element 1 includes, in addition to titanium oxide and tin oxide mentioned above, cobalt oxide (CoO), manganese oxide (MnO), zinc oxide (ZnO) and cupric oxide (CuO), and any of those metal oxides may be used as the material of the gas component sensor element 1.

While the gas component sensor element for producing the electrical signal in accordance with the gas component in the gas under test, shown in the above embodiments, is constructed by the metal oxide such as titanium oxide the electrical resistance of which changes in accordance with the gas component, it may be constructed by a metal oxide such as zirconium oxide an electromotive force of which changes in accordance with the gas component. When such a gas component sensor element constructed by the zirconium oxide, a groove for bringing atmosphere into contact with one surface of the gas component sensor element must be formed in the holder 2, and the gas component sensor element and the holder 2 must be hermetically sealed at the junction thereof to prevent the gas under test from entering the atmosphere side of the gas component sensor element.

What is claimed is:

1. A gas component sensing apparatus comprising:
   a solid state electrolyte made of metal oxide having an electrical resistance which changes in accordance with a gas component in a gas under test;
   a holder made of heat resistive, electrically insulative metal oxide and having an axially extending through-hole formed therein, said solid state electrolyte being held at one end of said through-hole;
   a lead member of conductive material fixed to the other end of said through-hole of said holder;
   a housing of conductive metal fixed around the outer periphery of said holder;
   a pair of electrodes formed on opposite surfaces of said solid state electrolyte in such a manner to prevent electrical shortcircuit therebetween;
   a first electrically conductive path means arranged in said through-hole of said holder for electrically connecting one of said pair of electrodes with said lead member; and
   a second electrically conductive path means formed in a thin film structure on the outer surface of said holder for electrically connecting the other electrode with said housing; whereby the change in said electrical resistance of said solid state electrolyte is taken across said lead member and said housing.

2. A gas composition sensing apparatus according to claim 1 wherein said electrodes comprises a pair of thin film metal layers.

3. A gas composition sensing apparatus according to claim 1 wherein one of said pair of electrodes comprises a conductive metal wire and other electrode comprises a metal layer.

* * * * *